United States Patent [19]

Pappas

[11] Patent Number: 5,507,820
[45] Date of Patent: Apr. 16, 1996

[54] FIXED BEARING JOINT ENDOPROSTHESIS

[75] Inventor: Michael J. Pappas, Caldwell, N.J.

[73] Assignee: Biomedical Engineering Trust I, South Orange, N.J.

[21] Appl. No.: 182,675

[22] Filed: Jan. 14, 1994

Related U.S. Application Data

[63] Continuation of Ser. No. 989,821, Dec. 14, 1992, abandoned.

[51] Int. Cl.⁶ ........................................ A61F 2/38
[52] U.S. Cl. ............................................. 623/20
[58] Field of Search ........................ 623/20, 18

[56] References Cited

U.S. PATENT DOCUMENTS

| Re. 29,757 | 9/1978 | Helfet | 623/20 |
| 5,203,807 | 4/1993 | Evans et al. | 623/20 |

FOREIGN PATENT DOCUMENTS

| 2253147 | 9/1992 | United Kingdom | 623/20 |

*Primary Examiner*—David H. Willse
*Attorney, Agent, or Firm*—Anthony J. Casella; Gerald E. Hespos

[57] ABSTRACT

Joint endoprostheses, disclosed in the context of a total knee prosthesis, incorporate a first element for rigid connection to a first bone, the first element having an articulating surface; a second element for rigid connection to a second bone, the second element having a bearing surface which engages the articulating surface; wherein the engagement of the articulation surface with the bearing surface at any degree of relative rotation therebetween is reflected by a substantially constant contact configuration, the relative rotation of the device being accompanied by displacement of the bones toward and away from each other.

10 Claims, 12 Drawing Sheets

FIXED BEARING JOINT ENDOPROSTHESIS

This is a continuation of U.S. application Ser. No. 07/989,821, filed on Dec. 14, 1992, now abandoned.

BACKGROUND OF THE INVENTION

This invention relates to joint endoprostheses and, more specifically, to joint endoprostheses having one prosthetic element fixed to a first bone, e.g., a distal femur, and a second prosthetic element fixed to a second bone, e.g., a proximal tibia, each of the prosthetic elements having surfaces of engagement which are in contact with each other particularly during relative movement between the two bones.

It is generally recognized that there are three general categories of contact between the articulating surfaces of joint endoprostheses; theoretical point contact, theoretical line contact and area contact. Theoretical point contact occurs where adjacent bodies, not under load, i.e., undeformed, are touching at a point. Theoretical line contact occurs where adjacent bodies not under load, are touching along a line. Theoretical area contact occurs when adjacent bodies, not under load, are touching over an area. It is also recognized that theoretical contact ordinarily is not achieved because most bodies in engagement are under load which causes deformation of the material in contact.

More specifically, it will be recognized that when prostheses are subject to loads, although there may be described to occur theoretical point contact between two engaging surfaces, there factually occurs deformation which results in the actual contact being over an area around the theoretical point which area may be referred to as being a contact configuration. The same is true with respect to theoretical line contact. Further, the closer that undeformed engaging surfaces are to being congruent, the greater the area contact which occurs as a result of deformation under load. For purposes of this application, the reality is that there is no true point contact, that there is no true line contact, and that areas of contact in theoretical point and line contacts increase under load as the configurations of engaging surfaces approach congruency, will not only be recognized but will be used to advantage.

With the exception of the mobile bearing joint prosthetics disclosed in our prior U.S. Patents, e.g. , U.S. Pat. No. 4,470,158, U.S. Pat. No. 4,309,778 and U.S. Pat. No. 4,340,978, as well as U.S. Pat. No. 4,085,466, most known joint endoprostheses are typified by highly incongruent contact. The less congruency the greater the contact stresses which are produced under load. Often the stresses experienced in known joint prostheses exceed the acceptable limits associated with known bearing materials such as ultra high molecular weight polyethylene (UHMWPe) which is normally used in these applications. This problem is discussed in detail in our study which was published in 1987. Pappas, M. J., Marcus, G. and Buechel, F. F. "Evaluation of Contact Stresses in Metal-Plastic Total Knee Replacements," Biomaterials and Clinical Applications, p. 259, Elsevier Science Publishers B.V. Amsterdam, 1987.

Known joint prosthetics having fixed bearing surfaces as distinguished from mobile bearing designs, experience high levels of incongruency. Incongruent contact is inherent in such fixed bearing designs since knee motion is highly mobile and includes flexion-extension, axial rotation, anterior-posterior translation, and adduction-abduction. The long standing dilemma for designers of fixed bearing knees is to effect a compromise between the conflicting requirements for joint mobility (which is accomplished by increasing surface contact incongruity and thus contact stress) and low contact stress (which requires high congruity and thus low joint mobility) to prevent rapid failure of the plastic used in current prosthetic joint articulations. The generally accepted approach to resolving this dilemma has been to design prostheses which mimic as closely as possible, the design and operation of the natural knee.

Unfortunately, a satisfactory compromise has yet to be found where fixed bearing knee components can be considered safe for extended use under normal physiological loads. For current metallic and plastic materials used in joint replacement, only mobile bearing elements are capable of normal knee motion with contact stresses such that the plastic bearings appear capable of supporting normal physiological loads over an extended period of time.

There are patients, however, whose ages and/or infirmities are such that loads which they might produce in their generally restricted day-to-day activities are significantly less than the loading to be expected from a normal adult. These lower loading levels which produce lower contact stresses for a given articulation geometry, coupled with the reduced time and frequency of use ordinarily associated with the aged or infirm which reduce the likelihood of bearing damage for given contact stresses, permit the use of articulating surfaces which have a greater degree of incongruity, e.g., prostheses having fixed bearing components.

As compared to mobile bearing prostheses, fixed bearing prostheses need not utilize a supporting prosthetic platform, i.e., the bearing element can be fixtured directly to the bone. By eliminating the relatively expensive supporting platform, the cost of the prosthesis is reduced substantially, a clearly desirable benefit in these days of continuing efforts to reduce medical costs while producing adequate care. Since a low cost, fixed bearing device can be used in joint prostheses, e.g., as tibial or patellar components of a total knee in an elderly, inactive or infirm patient, the added costs of multipart tibial or patellar replacements often are not justifiable if a lower cost design is adequate.

Thus there has been a need for a joint endoprosthesis which is structurally and operationally adequate and safe for lower load applications and which is lower in cost than known joint prosthetics which are capable of handling typical loading from active adult patients. There also is a need for such low-cost joint endoprostheses which are suitable for use where there is no retained cruciate ligamenture and where such ligamenture is retained. It is the object of the invention to produce such prostheses in the context of a fixed bearing endoprosthesis.

SUMMARY OF THE INVENTION

The joint endoprosthesis of the present invention includes a first element for mounting on a first bone and having an articulating surface, and a second element for mounting on a second bone and having a bearing surface for cooperating with the articulating surface of the first element to permit articulation between the two elements to accommodate relative movement between the two bones. The articulating surface of the first element is a compound surface of revolution generated by revolving a generating curve. The articulating surface of the second element may be a Helicoid or compound Helicoid surface generated by simultaneously translating and rotating a revolving generating surface.

The resulting cooperating articulating surfaces although not providing totally congruent contact, provide an improved contact area under load throughout joint articulation involving flexion-extension, even when combined with axial rotation, which articulations are normally experienced together in the natural human gait. Thus, the present invention substantially lowers contact stresses during ordinary loading as compared with known incongruent fixed bearing devices with similar mobility. Lowering the contact stresses in incongruent fixed bearing devices reduces wear and fatigue damage of the prosthetic articulating surfaces, increasing the service life. Additionally, the ability of the improved fixed bearing design to withstand operating stresses increases the population group who can take advantage of the lower cost of their prostheses.

BRIEF DESCRIPTION OF THE DRAWINGS

A more complete understanding of the present invention can be had from the following detailed description, particularly when read in light of the accompanying drawings, wherein.

DETAILED DESCRIPTION

Figure 1:
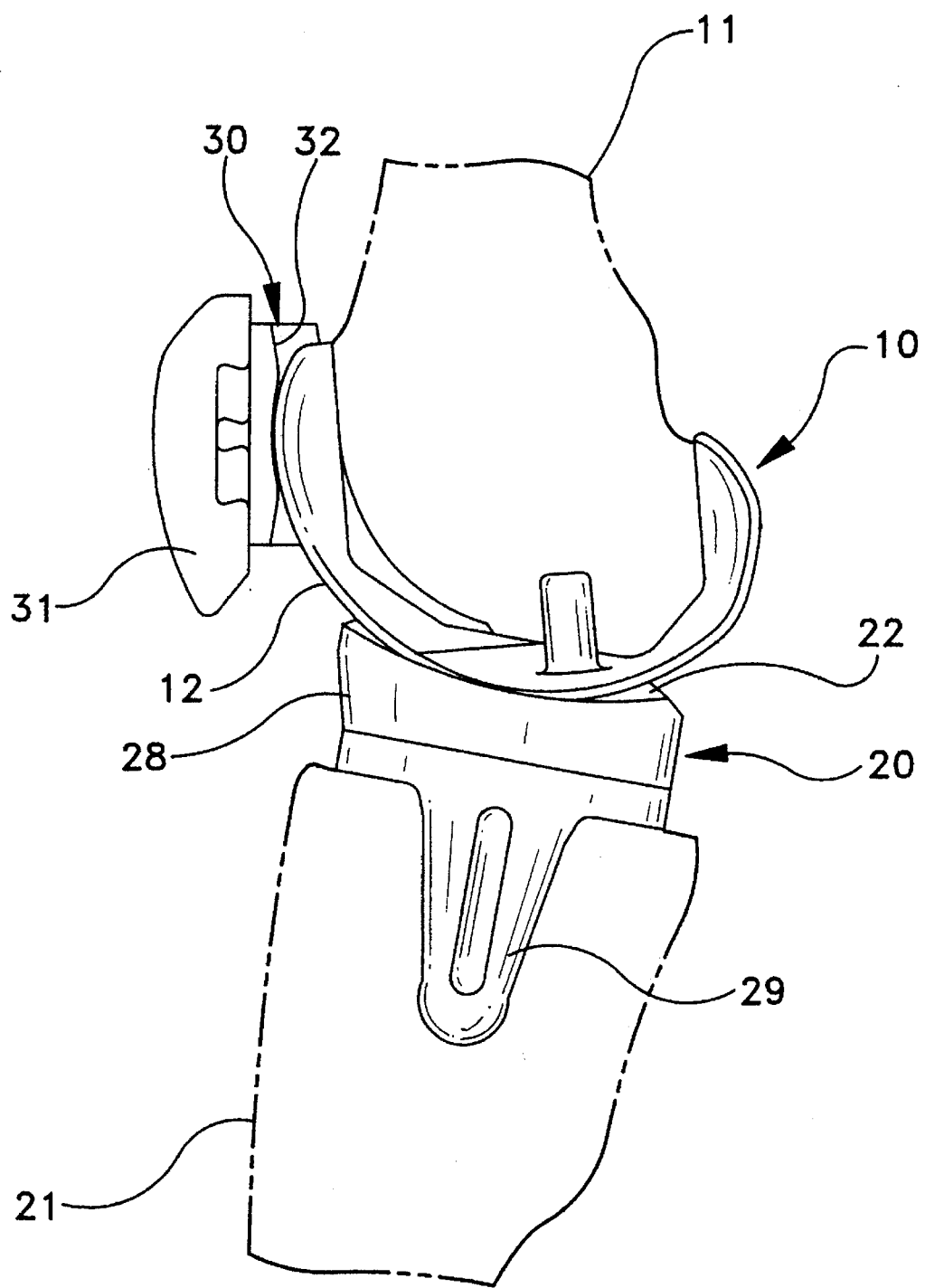
FIG. 1 is a side elevational view of an implanted total knee prostheses according to the invention including a patella component, the prostheses being shown fixed to bones which are depicted in phantom lines.
Figure 2:
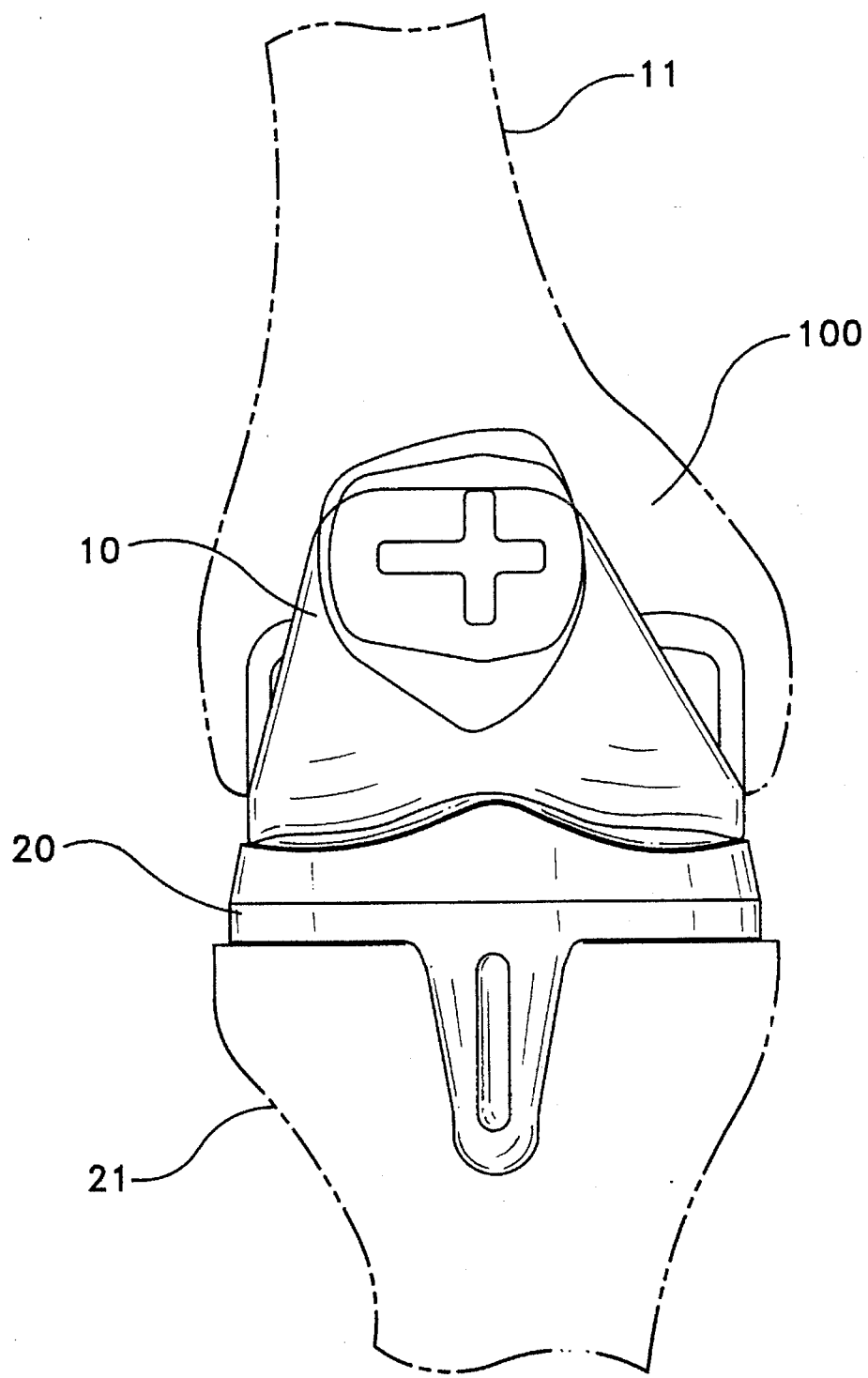
FIG. 2 is a front elevational view of the total knee prosthesis of FIG. 1.

Referring therefore to FIGS. 1 through 5, one embodiment of a joint endoprosthesis according to the present invention is shown in the context of a total knee replacement prosthesis, specifically designed for use where there are no cruciate ligaments. It also will be recognized that the joint endoprosthesis according to the invention may be used in other joint replacements including but not limited to ankles, knuckles and elbows.

The prosthesis as shown in FIGS. 1-5 is depicted in the anatomical or neutral position of the knee, i.e. the position where the tibia is in full extension with respect to the femur.

The total knee replacement prosthesis shown in FIGS. 1 through 5 can be seen to include a femoral component 10 secured to the distal femur 11 and a tibial component 20 secured to the proximal tibia 21. Femoral component 10 may be manufactured from any of the generally known implant metals such as Cobalt Chromium or a Titanium alloy. The tibial component 20 may be manufactured from a suitable bearing material such as ultra-high molecular weight polyethylene (UHMWPe). The prosthesis also can be seen to include a patellar component 30 rigidly fixed to the posterior surface of the natural patella 31.

Figure 3:
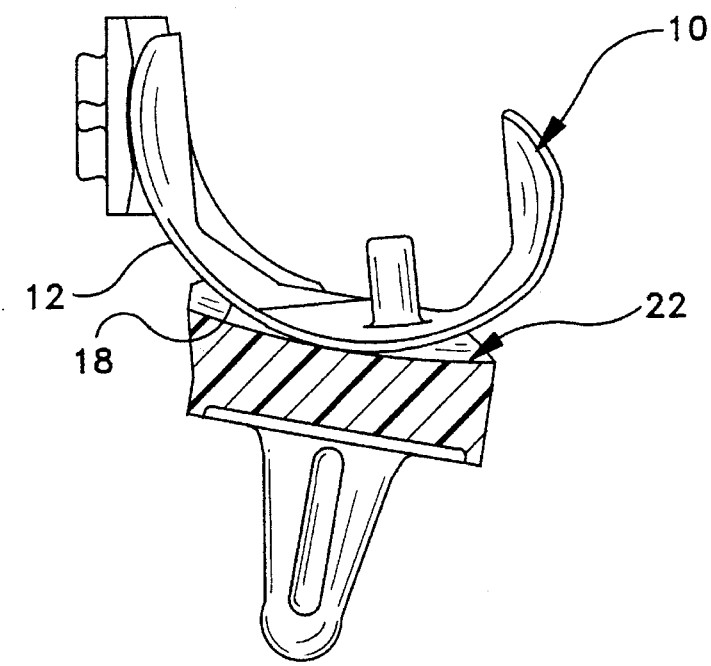
FIG. 3 is a view similar to FIG. 1 showing portions of the prosthesis in cross-section.
Figure 4:
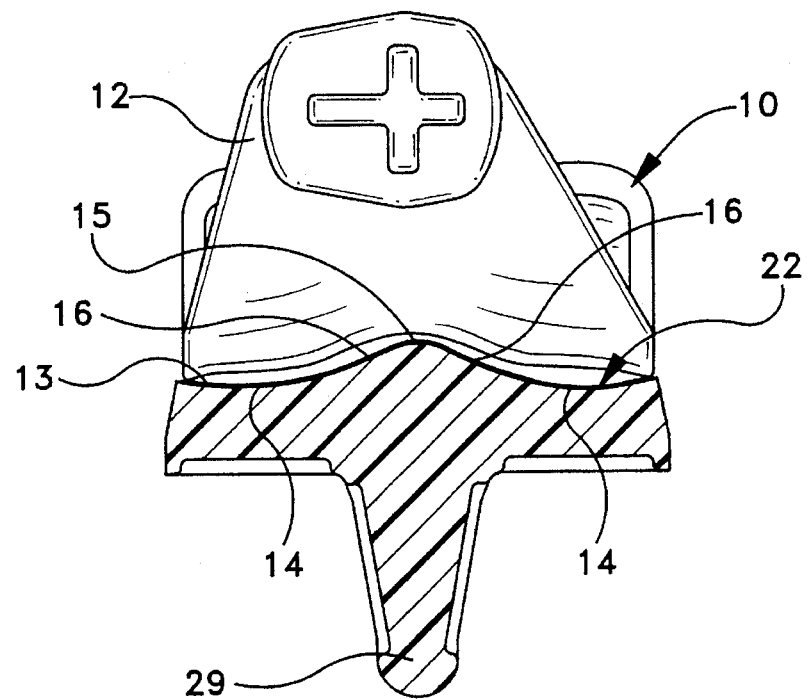
FIG. 4 is a view similar to FIG. 2 showing portions of the prosthesis in cross section.
Figure 5:
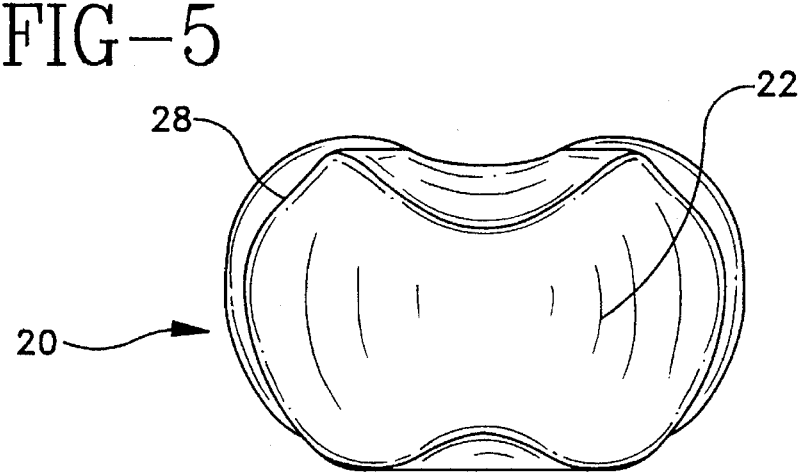
FIG. 5 is a top view of the tibial component of the prosthesis of FIG. 1.

Femoral component 10 includes an articulating surface 12 which engages the bearing surface 22 of tibial component 20 and the bearing surface 32 of patellar component 30 during normal use. The geometry of the articulating surface 12 of femoral component 10, as best may be seen in FIGS. 3 and 4, is a compound surface of revolution generated by revolving a generating curve 13 including radii 14, radius 15 and connecting tangents 16. In this regard the femoral component 10 of this invention may be substantially identical to the structure of femoral component 100 as disclosed in detail in our U.S. Pat. No. 4,470,158, the disclosure of which is incorporated herein by reference.

The tibial articulating bearing surface 22 of the present invention may be generated using a generating surface which is produced by a generating curve which is the same as or similar to generating curve 13. However, tibial articulating surface 22 is neither a standard surface of revolution nor a compound surface of revolution, i.e., a surface consisting of more than one connected surfaces of revolution. Rather, tibial articulating surface 22 is a Helicoid surface, i.e., a surface generated by simultaneously rotating and translating a surface of revolution. This generation method and the Helicoid or a Compound Helicoid surface defined thereby are both novel and particularly useful in providing the low cost joint prosthesis defined by the present invention.

The tibial component 20 in the embodiment shown is a one piece structure of UHMWPe having an upper platform section 28 and a depending spike 29 which facilitates securing the component 20 to tibia 21. Tibial component 20 may be manufactured by forming a tibial component blank 23 (FIGS. 6 and 7) by known techniques such as machining and molding or the like. The blank is then secured in an appropriate position for being worked by a revolving cutting tool The cutting surface 26 of cutting tool 24 for the embodiment of FIGS. 1-5 is made in the form of a surface of revolution corresponding to the geometry of articulating surface ]2 of femoral component 10.

Figure 6:
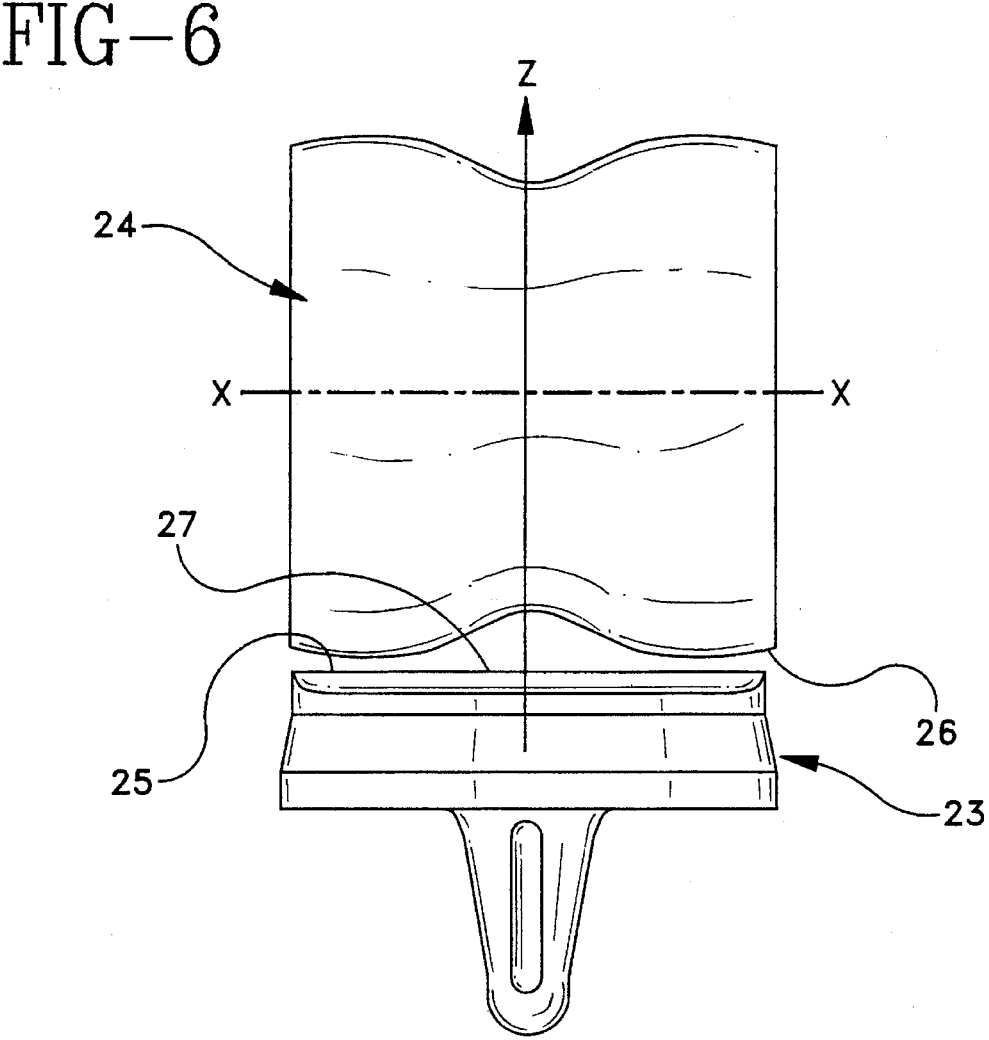
FIG. 6 is a front elevational schematic view of a tibial component blank and a tool for forming the bearing surface of the present invention.
Figure 7:
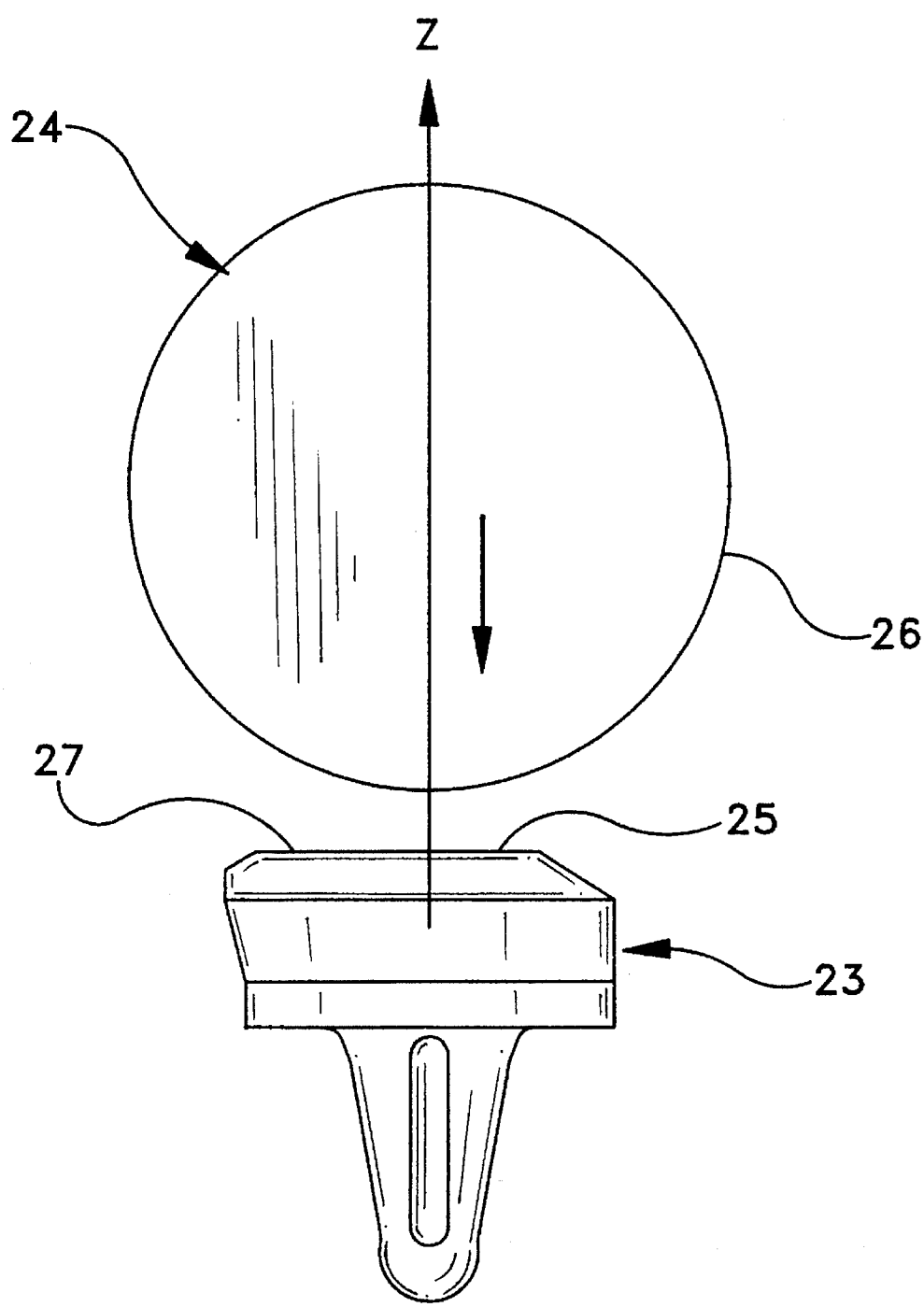
FIG. 7 is a side elevational view of the structure shown in FIG. 6.

Tool 24 revolves rapidly about axis X—X which is parallel to the plane 27 of the face of tibial component blank 23. Additionally, the tool 24 has a Z axis which bisects the tool from left to right as seen in FIG. 6, which passes through the axis of revolution X—X of the tool and which is perpendicular to the plane 27 of the face of blank 23. The Z axis is the axis along which tool 24 translates and about which tool 24 rotates in forming the novel Helicoid surface of the tibial component or bearing of this invention. In the embodiment of FIGS. 1–7, the Z axis is coincident with the central longitudinal axis of tibial component 20. However, as discussed below, it may be displaced therefrom.

Figure 8:
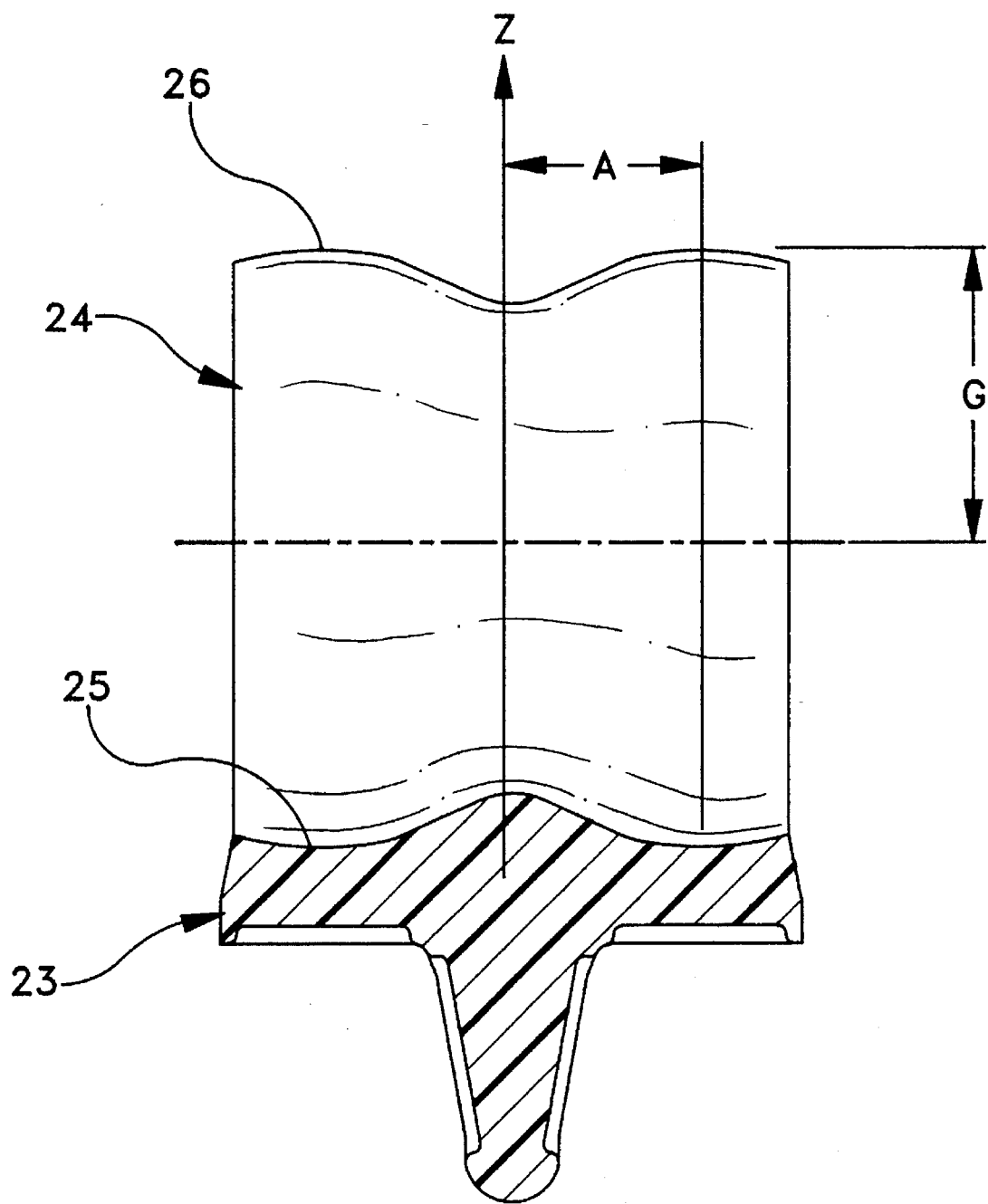
FIG. 8 is a view similar to FIG. 6 but showing the tool having been advanced into the blank during the process of forming the novel bearing surface.
Figure 9:
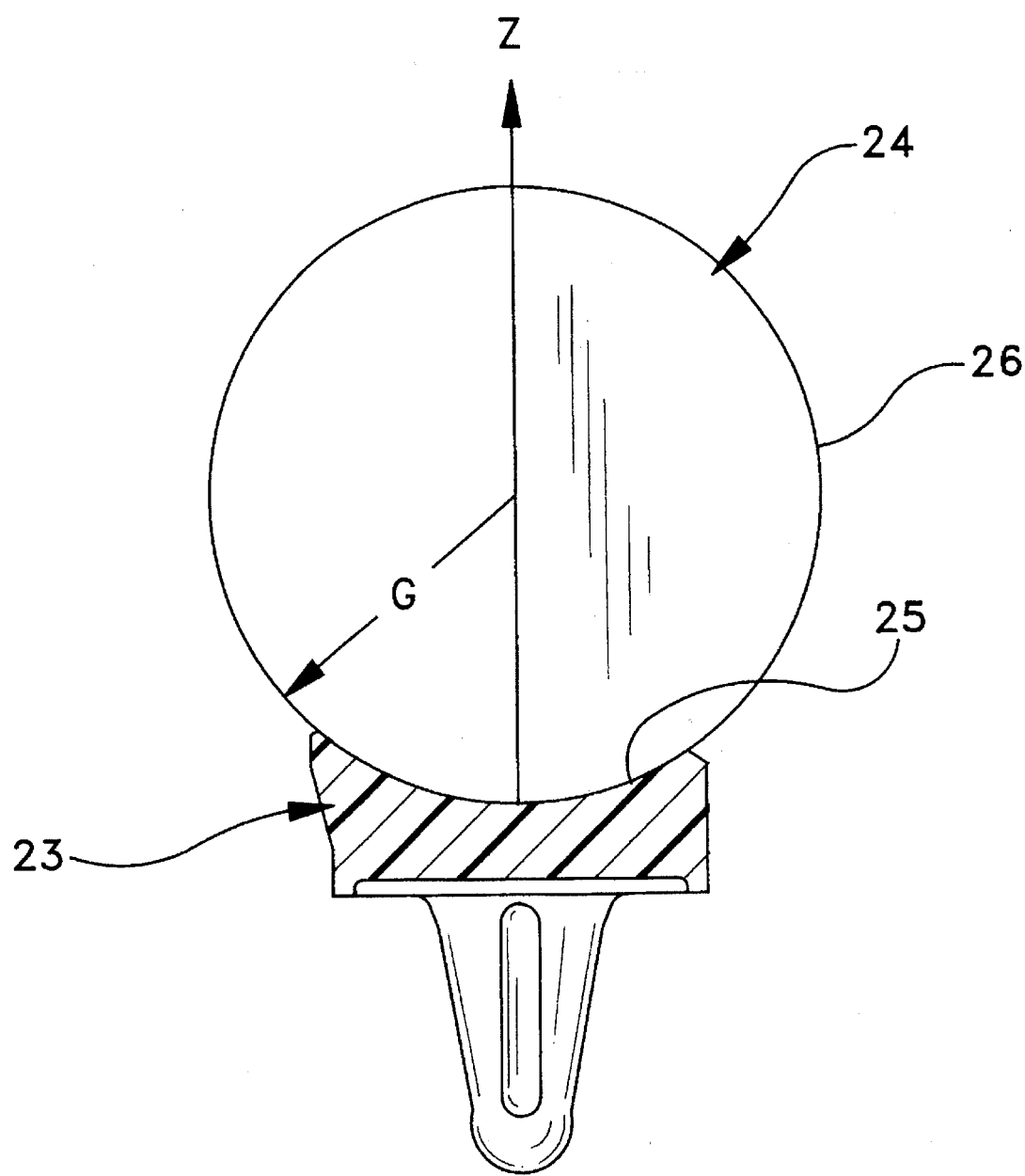
FIG. 9 is a side elevational schematic view at the structure shown in FIG. 8.

Thus in forming surface 12, the rapidly revolving cutter surface 26 of tool 24 is advanced against the surface 25 of blank 23 by translating tool 24 toward blank 23 along the Z axis. Translation is continued until the cutter surface 26 is in engagement with the full upper surface of blank 23 as is shown in FIGS. 8 and 9. At this position the axis of revolution X—X is located at the Z=0 position. It should also be noted that at this point in the forming operation no rotation of the tool 24 about the Z axis has occurred. Accordingly, in this position, with the angle of rotation of tool 24 being designated as $\Theta$, the position of tool 24 with respect to blank 23 is Z=0, 0=$\Theta$.

As will be recognized by those skilled in these arts, this first cut results in the formation of a surface on the tibial component which is the reverse of the surface 26 of tool 24. However, in order to achieve the Helicoid surface of the novel bearing of this invention, the following additional manufacturing steps are taken. With cutting tool 26 continuing to rapidly revolve around axis X—X, it is translated upwardly from the Z=0 position while at the same time being rotated about the Z axis. Clockwise rotation of the tool as seen from the top is positive $\Theta$ rotation and causes the tool to form the left rear quadrant and the right front quadrant of the finished Helicoid bearing surface. Upon completion of formation of these two surfaces, the tool is rotated and translated back to the Z=0, O=$\Theta$ position and once again translated upwardly from the Z=0 position while at the same time being rotated in a counterclockwise direction (negative $\Theta$ rotation) to form the left front and right rear quadrants of the Helicoid bearing surface.

The amount of translation Z along the Z axis is a function of the amount of rotation $\Theta$ of the cutting tool 24, i.e., Z=f($\Theta$). In both positive and negative $\Theta$ rotations, the simultaneous rotation and translation continue until the cutting surface 26 of tool 24 no longer engages the upper surface of tibial element 20. These positions of disengagement may be designated $\Theta=\Theta_1$ and $\Theta=-\Theta_1$.

Figure 10:
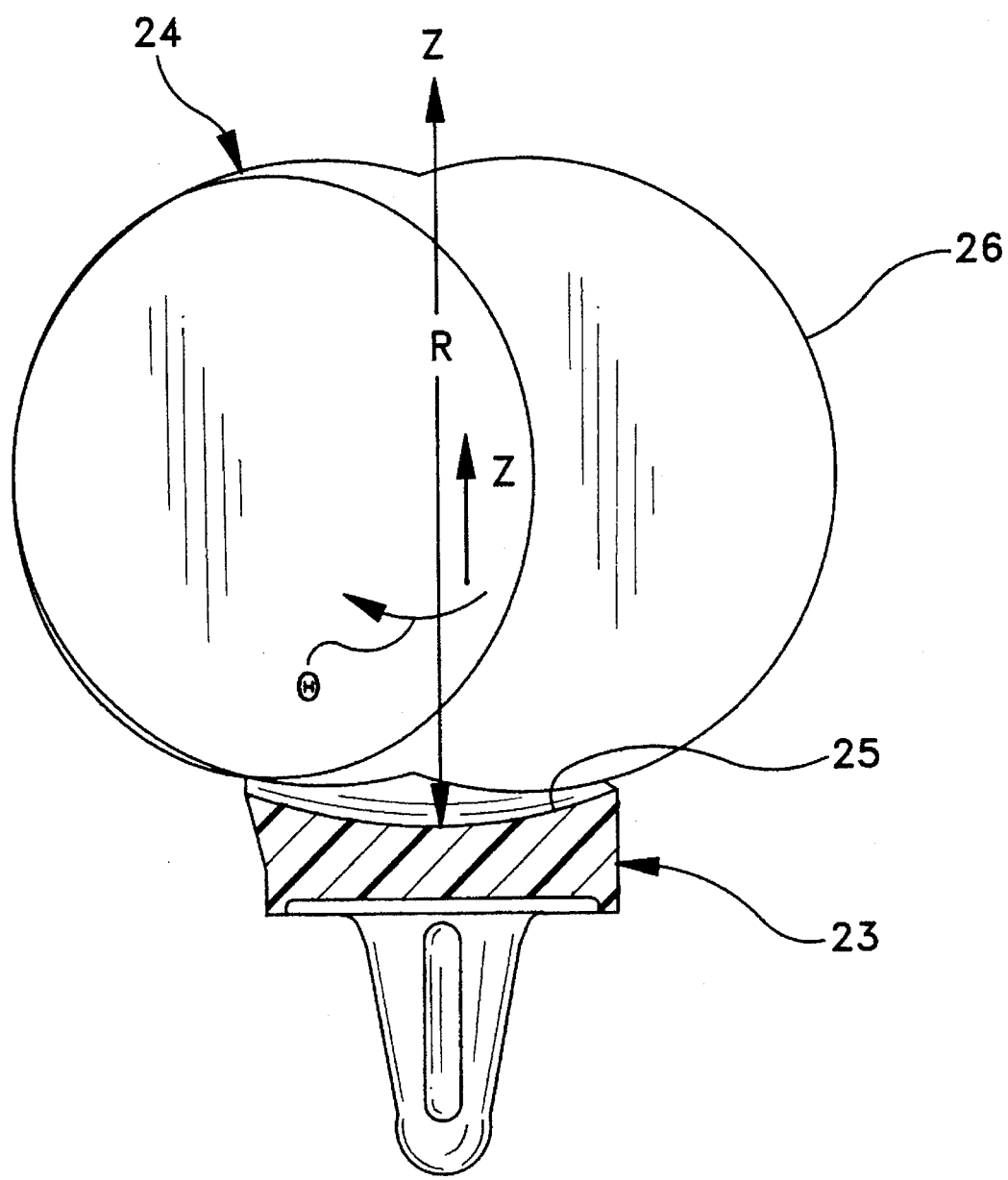
FIG. 10 is a view similar to that of FIG. 9 but showing the tool during translation and rotation in forming the bearing surface according to the invention.

The relationship between translation (Z) and rotation ($\Theta$) for a Helicoid surface resulting from the foregoing manufacturing operation is defined by the equation:

$$Z = B - [B^2 (A\Theta)^2]^{1/2} \tag{1}$$

where Z is the position of the X—X axis above Z=0, A (FIG. 6) is a surface parameter equal to the distance from the Z axis to a plane which contains the largest outside diameter G (FIG. 8) of the cutting surface 26 of tool 24, and B is equal to R−G where R (FIG. 10) is a surface parameter equal to the desired lateral radius of curvature of the resulting articulating surface. This resulting surface is the surface of a volume swept by the simultaneous rotation and translation of a body where, when the surface of the body is a surface of revolution, the axis of rotation is not coincident with the axis of the surface of revolution, and where equation (1) is not the equation of a straight line (a helix). The curve of intersection of a cylinder with axis Z and radius A, and the Helicoid surface, will have a local principal radius of curvature R, at all points on the intersection curve in a plane tangent to the cylinder at these points. Viewed in another way, R is the radius of the intersection curve in a plane formed by unwrapping the cylinder into the plane.

The Helicoid surface 12 also may be formed by starting tool 24 at the rotated position corresponding to $\Theta=\Theta$. and thereafter translating and rotating the tool through $\Theta=\Theta_1$, Z=0 to $\Theta=-\Theta_1$, Z=0 to O=−0. position. Many other techniques may be used to so form the surface however its disclosure in the context of the surface of revolution of tool 24 is considered to be most helpful.

Considering now the cooperation of the articulating surface 12 of femoral component 10 with the bearing surface 22 of tibial component 22, it first must be recognized that each surface is formed based upon the same surface of revolution. Thus, when the femoral and tibial components are disposed in the anatomical or neutral position, their engagement is one of theoretical line contact across the entire width of femoral component 10 (FIG. 4). In reality, under load, there will be an area of contact defining a contact configuration based upon the amount the bearing surface 22 of tibial element 20 is deformed by the load thereon from the articulating surface 12 of the femoral element 10.

In the course of natural knee movement, e.g. in the course of flexion or extension, the tibia tends to rotate with respect to the femur. Such rotation would be reflected in the present invention by relative rotation between the femoral and tibial components about the Z axis of the tibial component. Such rotation may also occur during unnatural knee movement, e.g. where the person's foot may be planted and his body turns. Relative rotation between the tibia and femur in the natural knee best may be described as the lateral portion of the tibia rotating about an area of contact between the medial surfaces of the femur and tibia. The anatomy of the natural knee is such that such rotation from the anatomical or neutral position in either direction is not accompanied by a displacement or translation of the tibia and femur toward or away from each other. Thus, conventional wisdom in knee prosthetic design would dictate that relative rotation from the neutral position be accommodated by a system which does not result in separation of the tibial and femoral components.

The present invention, however, rejects the conventional wisdom and in doing so achieves reduced contact stresses and reduced incidence of bearing failure. Thus, in the embodiment of FIGS. 1–5, relative rotation between the femoral and tibial and femoral components from the anatomical or neutral position causes the tibial and femoral components to be displaced axially from each other. Where no cruciates are present the only limiting factor to such displacement is the tightness of the collateral ligaments. Ordinarily such ligaments limit displacement to approximately four millimeters (4 mm). Where the posterior cruciate is present the displacement can be expected to be limited to approximately one and one-half millimeters (1-½ mm). Accordingly, the Helicoid surface of the present invention has been designed to cause axial displacement of one and one-half millimeters (1-½ mm) over a rotation of thirty degrees (30°) in either direction from the neutral position, i.e., to position where $\Theta=30°$ or $\Theta=-30°$.

When the tibial and femoral components rotate away from the anatomical or neutral position, the movement of the articulating surface of the femoral component with respect to the bearing surface of the tibial component traces the movement of the cutting tool in forming the Helicoid surface. Thus, substantially the same theoretical line contact or contact configuration is maintained throughout the rotation thus maintaining the contact stresses at acceptably low levels. In this regard, the contact stress to be experienced with the structure of the present invention should not exceed approximately twelve 12 MPa pascals during peak loading of the prostheses during normal gait. This compares with the typical stresses calculated for known fixed bearing devices in the range of twenty to sixty (20 to 60) MPa over comparable ranges of rotation. Such contact stresses are unacceptable and in fact cannot occur because the yield point of the conventional bearing material (UHMWPe) is approximately thirty (30) MPa. Thus, there can be expected and there have occurred occurrences of permanent deformation in the bearing material of known devices under these conditions. Clearly this is unacceptable.

Thus, by accepting the axial displacement, the bearing surface can be formed as a concave surface such as closer to approach tile geometry of the articulating surface of the femoral component. This surface relationship permits the reduction in contact stresses which is desired and still accommodates the required function of the joint.

Figure 11:
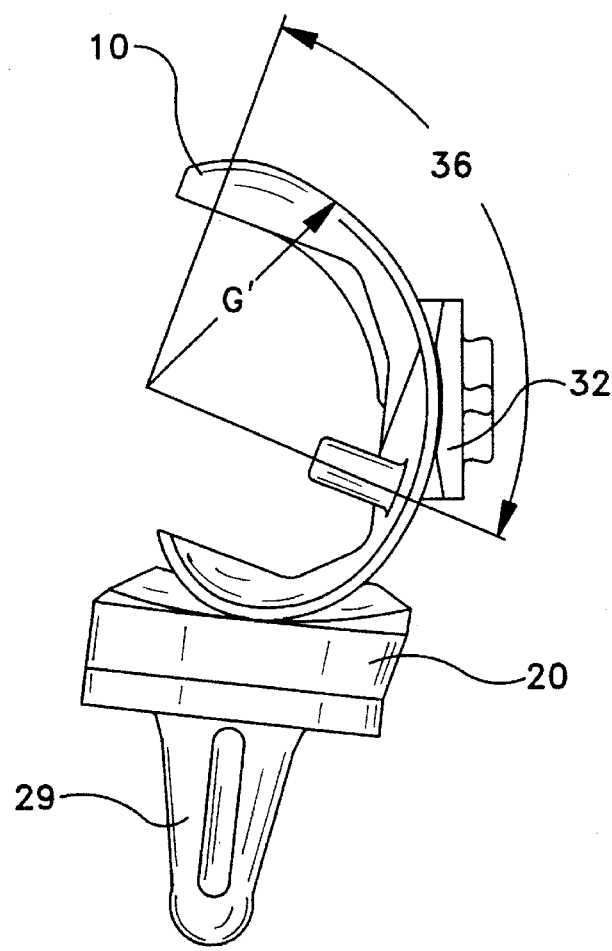
FIG. 11 is a side elevational view, partly in cross-section of a prosthesis according to the invention and in particular the relationship between the femoral bearing surface and the patella.

Further considering the nature of the formation of this surface it can be seen that, in the absence of rollback which occurs when the posterior cruciate or both cruciates are present in the natural knee, the combination of flexion-extension and axial rotation of the prosthetic joint will result in theoretical line contact between the bearing surface 22 of the tibial component and the articulating surface 12 of the femoral components where incongruity is limited by the difference in radius G' (the segment radius in the formation of articulating surface 12 as seen in FIG. 11, which represents the primary load bearing area) and radius R. For the embodiment shown the incongruency ratio (R−G')/R is about 0.5. Earlier line contact devices such as the PCA and Whiteside knees using a surface of revolution (Z=O for all angles Θ) as the tibial articulation surface in effect use the above defined relationship where R is infinity. For such surfaces the incongruity ratio is unity. Thus the Helicoid surface of the bearing of the present invention increases the congruity of theoretical line contact from bearing edge to bearing edge at all normal knee positions and therefore substantially reduces contact stresses. Using the contact stress equations in the Pappas, Makris and Buechel reports cited above, the computed stress for the prostheses of the invention would be less than half of the best of the incongruent designs evaluated. Indeed the Helicoid surface of the bearing of the present invention cooperates with the articulating surface 12 of the femoral element to provide a higher degree of theoretical line contact even during relative rotation between the bearing and the femoral components with attendant displacement of the femur and tibia toward and away from each other. Further, the area of contact reflected by the theoretical line contact remains substantially constant during rotation under constant load.

The use of the Helicoid surface of the bearing of the present invention in knee replacements where the cruciate ligaments are absent can produce articulations with less incongruity than where these ligaments are present. Where cruciate ligaments are present, the tendency to anterior-posterior translation of the femur relative to the tibia during flexion/extension in known devices tends to force theoretical point rather than theoretical line contact between the articulating surfaces, increasing contact stress and the likelihood of surface damage. The present Helicoid surface, however will produce a more congruent articulation than a surface of revolution with similar joint mobility characteristics. However, the Helicoid bearing surface of the invention clearly is most effective in knee replacement devices where the cruciate ligaments are absent.

Where the posterior cruciate ligament is present, improved congruency can be achieved by utilizing a Compound Helicoid surface according to the present invention, all as will be discussed below with respect to the embodiments shown in FIGS. 14–18.

Figure 12:
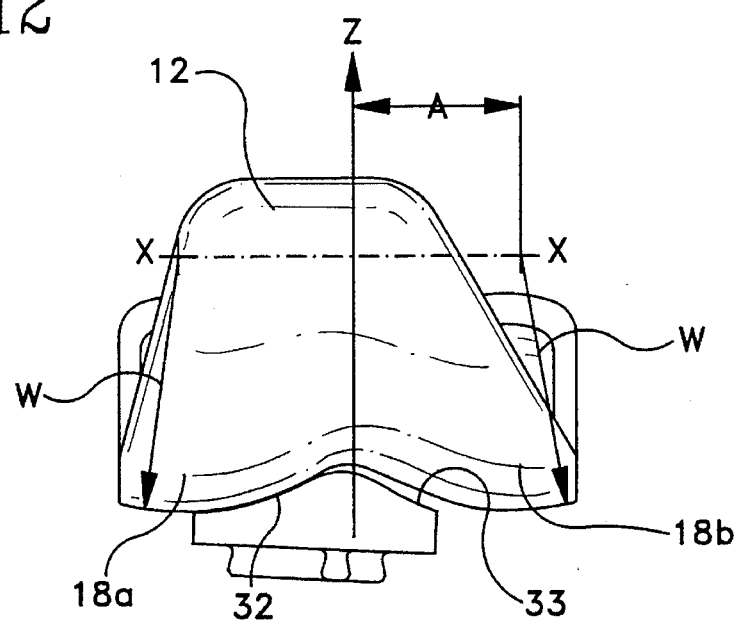
FIG. 12 is a top view of the structure of FIG. 11.
Figure 13:
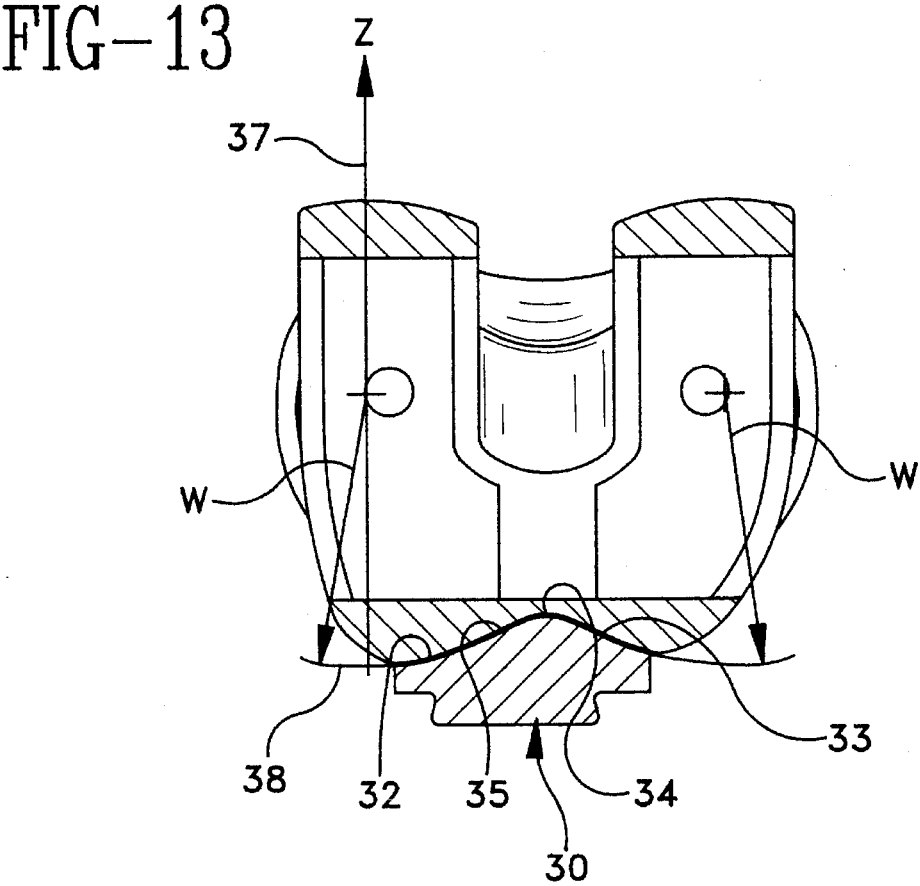
FIG. 13 is a cross-sectional view through the plane of 13—13 of FIG. 11.

As was noted above, the prosthesis of the present invention may include a patellar component 30 having a bearing surface 35 with a lateral portion 32 and a medial portion 33 which cooperate with articulating surface 12 of femoral element 10 (see generally FIGS. 11–13). It is generally known that the ordinary loads pressing patellar component 30 toward articulating surface 12 usually have a substantial lateral component. Thus, the lateral patellar articulation surface 32 of patellar component 30 carries most of the patellar load. In contrast, the medial patellar articulation surface 33 (FIGS. 12 and 13) from time to time lifts off the femoral component articulating surface (FIG. 12). If the generating radius (FIG. 11) of the primary load bearing segment 18 is equal to radii W as shown in FIGS. 12 and 13, segment 18 of the femoral articulating surface will contain a spherical surface. In this regard the lateral portion or region 18a of surface 18 and the medial portion or region 18b (FIG. 12) of surface 18 will each define a spherical surface. Thus, if the lateral patellar articulation surface 32 is of an identical spherical radius as the radius of spherical lateral portion 18a, the normal axial rotation of the patellar component 30 can occur with congruent contact when medial component 33 experiences lift-off. This is so even where the patellar component 30 is fixed to an axially rotating patellar remnant 31 (FIG. 1) since the contacting surfaces are spherical and thus allow rotation about three independent axes under congruent contact.

Where the lateral component of the patellofemoral compressive load is insufficient to produce lift-off of patellar articulation surface 33, as shown in FIG. 13, congruent articulation at the lateral patellar articulation surface 32 will still occur but articulation at the medial patellar articulation surface 33 will be incongruent. The nature of this incongruent contact can be improved to theoretical line contact if the entire patellar articulating surface 35 is a surface of revolution or a Helicoid surface generated by rotating axis X—X about a Z axis positioned through the center of lateral radius W as shown in FIG. 13, i.e., displaced from the central longitudinal position discussed above with respect to FIGS. 6–9.

Where primary load bearing segment 18 of femoral articulation surface 12 is sufficiently large as to extend over the full range of motion 36 (FIG. 11) of the patellar prosthesis 30, i.e., the area where there is significant loading at the patellofemoral interface, then the congruent lateral contact will occur over this range of motion. In this regard, it can be seen that patellar articulation surface 35 and tibial articulating surface 22 share a common generating curve 13 with the femoral articulating surface 12 since both the patellar and tibial articulations occur over segment 18.

Figure 14:
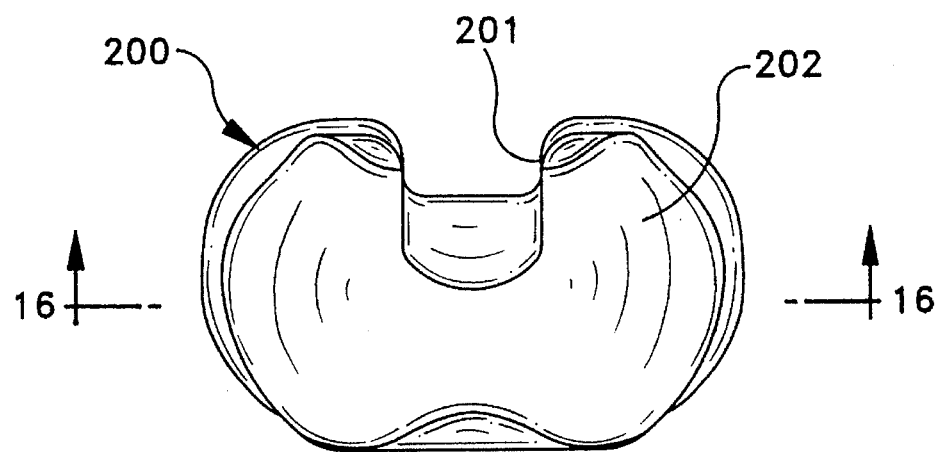
FIG. 14 is a top view of the bearing element of a second embodiment of prosthesis according to the present invention.
Figure 15:
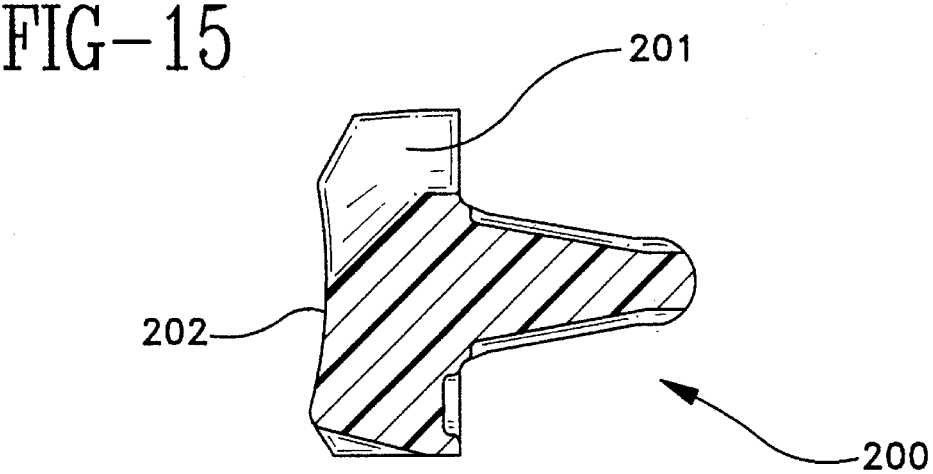
FIG. 15 is a side cross-sectional view through the plane 15—15 of FIG. 14.
Figure 16:
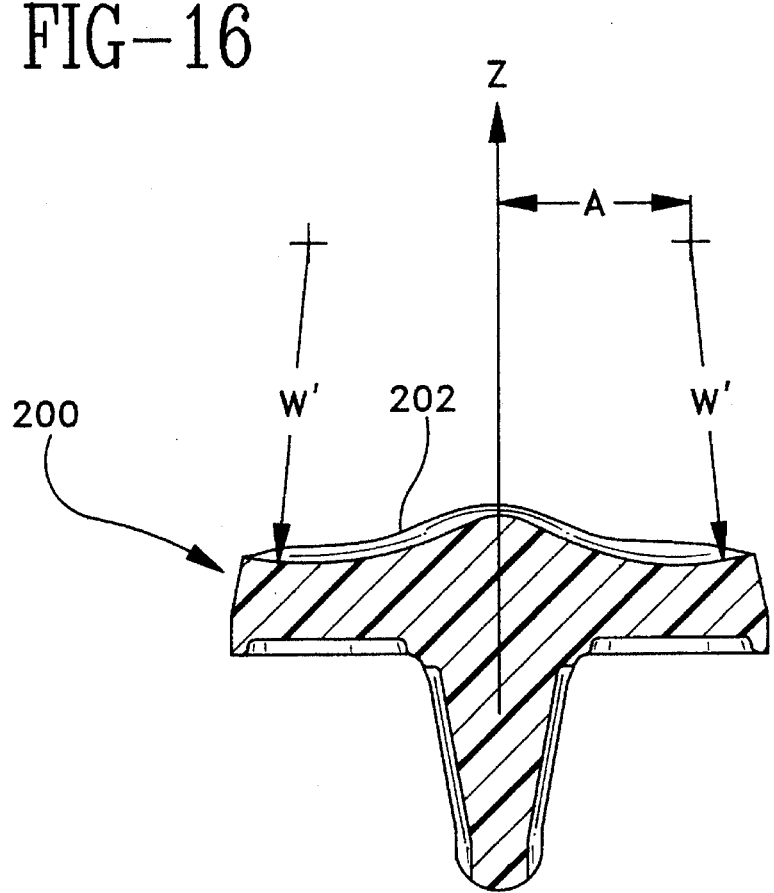
FIG. 16 is a front elevational cross-sectional view through the plane 16—16 of FIG. 14.

Referring now to FIGS. 14–16 a second embodiment of tibial element according to the invention is designated generally by reference numeral 200. Element 200 is designed for use where the patient's posterior cruciate ligament is retained. More specifically tibial element 200 is provided with a notch 201 formed in its posterior surface which accommodates the passage of the posterior cruciate ligament.

Because the presence of the cruciate ligaments cause anterior-posterior movement during flexion/extension, sometimes known as "roll back", the bearing surface 202 of component 200 is somewhat different than surface 22 of tibial component 20. More specifically, in component 200 the radii W are greater than radii W of tibial component 20.

Although this change in radius without any change in the articulating surface of the femoral component produces theoretical point contact and thus additional incongruity of the articulating surfaces, it does permit the necessary degree of mobility to accommodate the roll-back. A measure of the degree of incongruity may be made by comparing the radii and establishing a factor which may be called the "frontal incongruity ratio." This ratio represented by the designation F is stated as F=(W'−W)/W'. It has been found that a frontal incongruity ratio of about 0.2 accommodates about 10 mm of anterior-posterior movement which is normal in the human knee. Increasing the value of the ratio would provide additional mobility, but only at the expense of an unnecessary increase in contact stress.

Tibial component 200 may be manufactured by forming a blank having a notch and thereafter using a cutter to form surface 202 in the same manner as discussed with respect to tibial component 20; the only difference is the difference in dimensions of radii W and W'.

Additionally, the tibial component may be provided with a deeper notch to accommodate the passage of both anterior and posterior cruciate ligaments. In such case the tibial element may be fixed to the tibia using multiple fixation posts.

Figure 17:
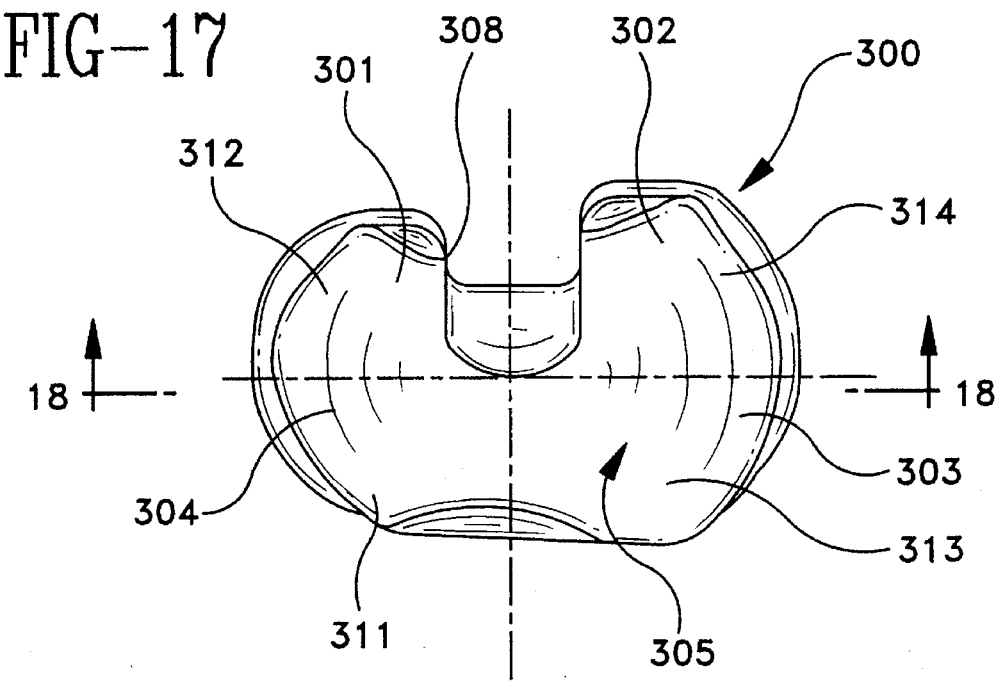
FIG. 17 is a top view of the bearing element of a third embodiment of prosthesis according to the present invention.
Figure 18:
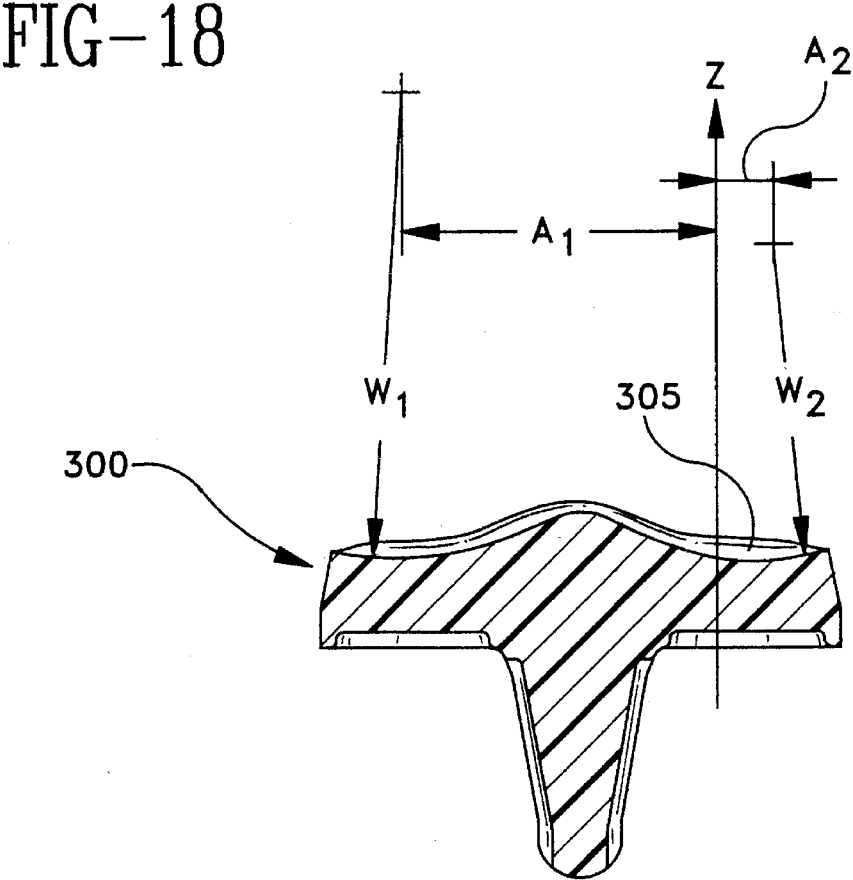
FIG. 18 is a front elevational cross-sectional view through the plane 18—18 of FIG. 17.

Referring to FIGS. 17 and 18 there is shown yet an additional embodiment of a tibial component structured in accordance with the invention and designated generally by reference numeral 300. Component 300 is the same basic structure as component 200 in that it has a cruciate accommodating slot 308, however the bearing surface 305 is asymmetrical when comparing its lateral side 301 with its medial side 302. This asymmetry better approximates the natural tibial shape, natural motion and loading characteristics of the human knee. Thus, the lateral side 301 of component 300 is smaller than the medial side 302. Normal knee roll-back of the femur on the tibia during flexion is about 5 mm on the medial side, i.e., in the medial compartment, and about 15 mm on the lateral side, i.e., in the lateral compartment. This condition allows less incongruency on the medial articulating surface 303 but requires more incongruency on the lateral articulating surface 304. This is also the case in the natural knee where the medial articulating surfaces of femur and tibia are more congruent than the lateral articulating surfaces. Thus it has been found to be a good compromise to sacrifice congruency to obtain additional mobility on the lateral side so as to obtain additional congruity on the medial side where the loads are higher. The added medial congruity is achieved by limiting mobility. However, because less mobility is needed, the limitation is not harmful.

Articulating surface 305 is formed using the same basic technique as described above but with a differently dimensioned cutting tool and a slightly modified cutting technique. More specifically, articulating surface 305 is produced by using a generating curve where $W_1$ (FIG. 18) is greater than W' (FIG. 16) which is greater than $W_2$ (FIG. 18) which in turn is greater than W (FIG. 13), and also where $A_1$ (FIG. 18) is greater than A (FIG. 12) which is greater than $A_2$ (FIG. 18). As best may be seen in FIG. 18, the Z axis for this embodiment is medially displaced from the center. The Helicoid surface resulting from forming in accordance with the foregoing parameters will provide more congruency on the medial side and less congruency on the lateral side. Further, the surface will accommodate less anterior-posterior motion on the medial side and greater anterior-posterior motion on the lateral side as compared with tibial component 200. For this embodiment, frontal incongruity ratios of about 0.1 and 0.3 for the medial and lateral sides respectively are considered to provide sufficient mobility. It should be noted that if $A_2$=O and $W_2$=W, then the medial bearing surface and the medial articulating surface will be spherically congruent.

It should be noted that a full width cutter such as cutter 24 (FIG. 6) need not be used to form both sides of the articulating surface 305 of tibial component 300. For example, a half width cutter can be simultaneously rotated and translated such that it cuts the anterior lateral quadrant 311 using a first set of parameters for R and A. The cutter could then be used to cut the posterior lateral quadrant 312 using a second set of parameters for R and A. This would produce two different Helicoid surfaces. If the generation of both medial and lateral sides is accomplished at the same values of Z and $\ominus$ and use a cutter with the same generating curve, the resulting compound surface will be smooth and continuous. Such a surface is referred to here as a Compound Helicoid surface. The surfaces of the anterior and posterior medial quadrants 313 and 314 can be similarly generated. Preferably larger values of R and A are used to form the posterior quadrants than are used to form the anterior quadrants. Thus, medial quadrants 313 and 314 which are not required to deal with large amounts of roll-back can be made more congruent than lateral quadrants 311 and 312 where more roll-back occurs. In this regard the anterior quadrants 311 and 313 can have an incongruency ratio of 0 while the posterior quadrants 312 and 314 can have such ratios of 0.1 and 0.3 respectively.

It will be recognized by those skilled in these arts that techniques other than that described with respect to cutter 24 may be used to form the Helicoid and Compound Helicoid surfaces of the present invention. Further, Helicoid and Compound Helicoid surfaces may be formed on prosthesis elements having plastic materials mounted on platform structures of materials other than plastic, e.g., metal.

It also will be recognized that many modifications and variations of the disclosed embodiments may be made without departing from the spirit and scope of this invention.

We claim:

1. A prosthesis for permitting articulation of adjacent bones, said prosthesis comprising:

a first element for rigid connection to a first bone, said first element having an articulating surface defined by a compound surface of revolution having a primary load bearing section;

a second element for rigid connection to a second bone, said second element having a central longitudinal axis and having a bearing surface for engagement with said articulating surface, said bearing surface of said second element being a Helicoid surface defined by rotating and translating said compound surface of revolution around and along the central longitudinal axis of said second element; and wherein said articulation of said adjacent bones includes flexion, extension and relative rotation, wherein at any position of relative rotation the engagement of said articulating surface and said bearing surface defines a contact configuration which is substantially constant for all degrees of relative rotation of said first and second elements and wherein all of the contact of said bearing surface for all said degrees of relative rotation is with said compound surface of revolution, said relative rotation being accompanied by displacement of said bones toward and away from each other.

2. A prosthesis according to claim 1 wherein the engagement of said articulating surface of said first element with said bearing surface of said second element defines theoretical line contact.

3. A prosthesis according to claim 1 wherein the engagement of said articulating surface of said first element with said bearing surface of said second element defines theoretical point contact.

4. A prosthesis according to claim 1 wherein the relationship between the rotation and translation of said surface of revolution is defined by the equation:

$$Z=B-[B^2A\Theta)^2]^{1/2}$$

wherein:

Z is the position of the axis of revolution of the surface of revolution above the position of that axis when the first and second elements are in an anatomical or neutral position;

$\Theta$ is the angle of rotation of the axis of revolution about said central longitudinal axis of said second element measured from the position of said axis of revolution when the first and second elements are in anatomical or neutral position;

A is a surface parameter equal to the distance from the axis about which said surface of revolution rotates, to a plane which contains the largest outside diameter G of said surface of revolution through its axis of revolution; and B is equal to R–G where R is a surface parameter equal to the desired lateral radius of curvative of the bearing surface.

5. A prosthesis according to claim 1 wherein said Helicoid surface engages the surface of said primary load bearing section.

6. A prosthesis according to claim 1 wherein said first element is for securing to a femur and said second element is for securing to a tibia.

7. A prosthesis according to claim 1 wherein said first element is for securing to a femur and said second element is for securing to a patella.

8. A prosthesis for permitting articulation of adjacent bones, comprising:

a first element for rigid connection to a first bone, said first element having an articulating surface;

a second element for rigid connection to a second bone, said second element having a central longitudinal axis and having a bearing surface formed on said second element for engagement with said articulating surface; and wherein the bearing surface of said second element is a Helicoid surface defined by the simultaneous translation and rotation of a generating surface around and along the central longitudinal axis of said second element.

9. A prosthesis according to claim 8 wherein said articulating surface of said first element is a compound surface of revolution having a primary load bearing section.

10. A prosthesis according to claim 1 wherein the relationship between the rotation and translation of said generating surface of revolution is defined by tile equation:

$$Z=B-[B^2-A\Theta)^2]^{1/2}$$

wherein:

Z is the position of the axis of revolution of the generating surface above the position of that axis when the first and second elements are in an anatomical or neutral position;

$\Theta$ is the angle of rotation of the axis of revolution about said central longitudinal axis of said second element measured from the position of said axis of revolution when the first and second elements are in anatomical or neutral position;

A is a surface parameter equal to the distance from the axis about which said generating surface of revolution rotates to a plane which contains the largest outside diameter G of said generating surface of revolution through its axis of revolution; and B is equal to R–G where R is a surface parameter equal to the desired lateral radius of curvature of the bearing surface.

* * * * *